(12) United States Patent
Zhou et al.

(10) Patent No.: US 6,228,996 B1
(45) Date of Patent: May 8, 2001

(54) PROCESS FOR EXTRACTING SWEET DITERPENE GLYCOSIDES

(76) Inventors: James H. Zhou, 32 Hallmark Hill Dr., Wallingford, CT (US) 06492; Weiping He, Mail Box 215 Guanxi Teacher University Shar Li Dian, Guilin City Guanxi, 541004 (CN)

( * ) Notice: Subject to any disclaimer, the term of this patent is extended or adjusted under 35 U.S.C. 154(b) by 0 days.

(21) Appl. No.: 09/256,066

(22) Filed: Feb. 24, 1999

(51) Int. Cl.$^7$ .................................................. C07H 15/24
(52) U.S. Cl. ......................... 536/18.1; 536/4.1; 536/128
(58) Field of Search .................................. 536/4.1, 18.1, 536/128

(56) References Cited

FOREIGN PATENT DOCUMENTS

| 0727492 | * | 8/1996 | (EP) . |
| 52-105260 | * | 9/1977 | (JP) . |
| 58-28245 | * | 2/1983 | (JP) . |
| 59-51261 | * | 12/1984 | (JP) . |
| 1604838 | * | 11/1990 | (SU) . |

OTHER PUBLICATIONS

Ulubelen et al., "Terpenoids from *Salvia Sclarea*," *Phytochemistry*, 36(4), 971–974 (Jul. 12, 1994).*

Ohtani et al. (I), "Labdane–Type Diterpene Glycosides from Fruits of *Rubus foliolosus*," *Chemical & Pharmaceutical Bulletin(Japan)*, 39(9), 2443–2445 (Sep., 1991).*

Hashimoto et al., "Effect of Capsianoside, a Diterpene Glycoside, on Tight–Junctional Permeability," *Biochimica et Biophysica Acta*, 1323(2), 281–290 (Jan. 31, 1997).*

Ohtani et al. (II), "Minor Diterpene Glycosides for Sweet Leaves of *Rubus Suavissimus*," *Phytochemistry*, 31(5), 1553–1559 (May 1, 1992).*

Budavari et al. (eds.), *The Merck Index*, 11th Edition, Merck & Co., Rahway, NJ, 1989, only p. 1387 supplied, see espically entry No. 8766 (Stevioside).*

Wood et al., "Stevioside. I. The Structure of the Glucose Moieties," *Journal of Organic Chemistry*, 20, 875–883 (Jul., 1955).*

DuBois et al., "Diterpenoid Sweeteners. Synthesis and Sensory Evaluation of Stevioside Analogues Nondegradable to Steviol," *Journal of Medicinal Chemistry*, 24(11), 1269–1271 (Nov., 1981).*

* cited by examiner

*Primary Examiner*—Gary Geist
*Assistant Examiner*—L. E. Crane
(74) *Attorney, Agent, or Firm*—Bachman & LaPointe, P.C.

(57) ABSTRACT

A process is provided for obtaining diterpene glycosides which process extracts such diterpene glycosides from plant or botanical material so as to provide a product which is high in content of such diterpene glycosides, and substantially free of bitter tasting tannins. This advantageously provides a product which can be used as a sweetener material.

23 Claims, 1 Drawing Sheet

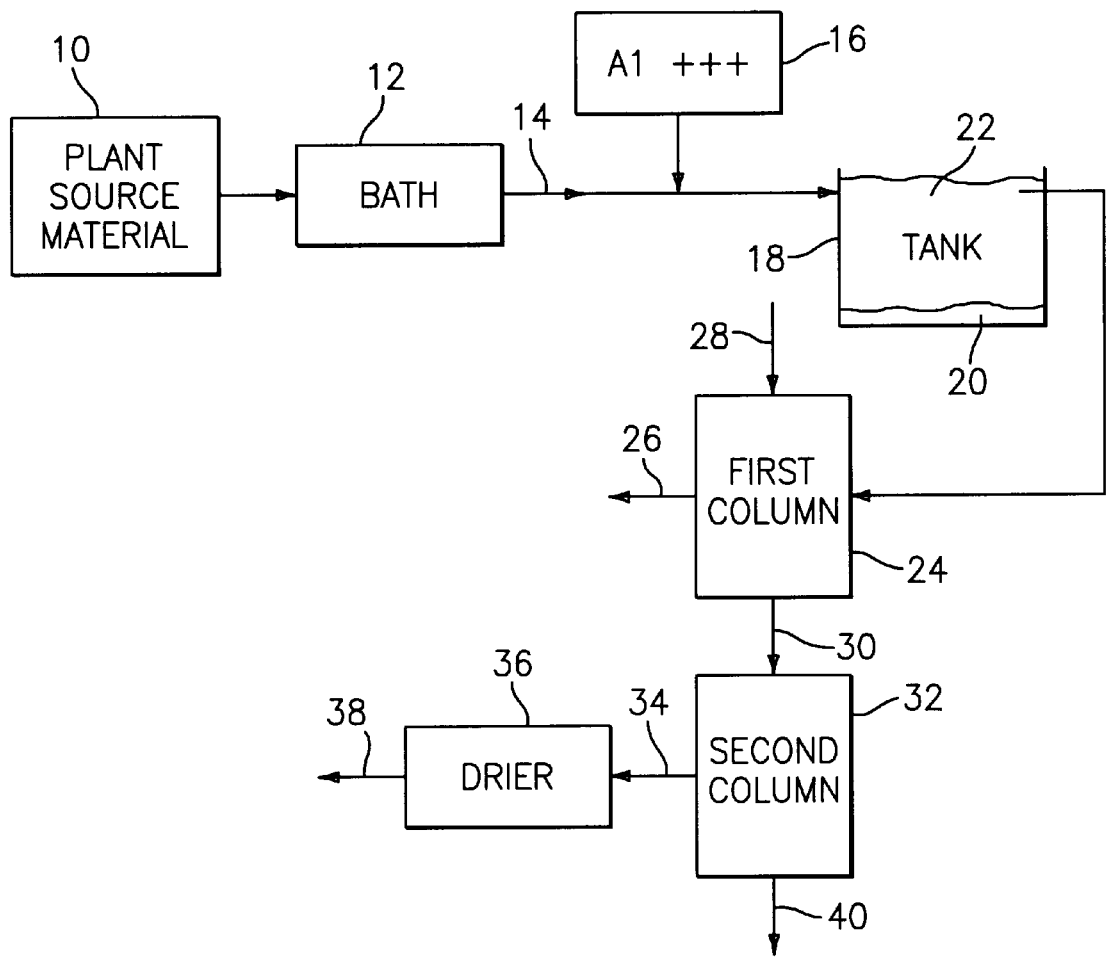
*FIGURE*

US 6,228,996 B1

PROCESS FOR EXTRACTING SWEET DITERPENE GLYCOSIDES

BACKGROUND OF THE INVENTION

The invention relates to a process for extracting diterpene glycosides from plant or botanical sources.

Diterpene glycosides are useful as naturally sweet material and can be obtained from various sources.

Typical plant or botanical sources contain useful diterpene glyocosides as well as certain additional polyphenolic substances, or tannins, some of which give health benefits such as anti-inflammation, anti-oxidation and the like. Other portions of these tannins, however, have an astringent or bitter taste, and render conventional extracts of such plant sources unsuitable for use as sweetening agents.

It is the primary object of the present invention to provide a process for extracting diterpene glycosides wherein the resulting product has a useful sweet flavor profile.

It is a further object of the present invention to provide a process for extracting diterpene glycosides which provides a highly concentrated diterpene glycoside end product.

It is a still further object of the present invention to provide a process for extracting diterpene glycosides which uses minimal amounts of organic or inorganic chemicals so as to provide a high yield of diterpene glycosides in an efficient, simple, consistent and economic process.

Other objects and advantages of the present invention will appear hereinbelow.

SUMMARY OF THE INVENTION

In accordance with the present invention, the foregoing objects and advantages have been readily attained.

According to the invention, a process for obtaining diterpene glycosides has been provided, which process comprises the steps of providing a plant source material containing diterpene glycosides, obtaining a liquid extract from said source material, said liquid extract containing said diterpene glycosides; mixing said liquid extract with a solution saturated with at least one metallic ion selected from the group consisting of metallic ions having an oxidation number of three, metallic ions having an oxidation number of two, and combinations thereof so as to provide a mixture; allowing said mixture to rest so as to provide a solid precipitate material and a liquid portion containing soluble portions of said liquid extract including said diterpene glycosides;

passing said liquid portion through a first column containing a neutral absorptive macroporous resin so as to absorb portions of said liquid portion including said diterpene glycosides onto said neutral absorptive macroporous resin; rinsing said first column with an alcohol so as to obtain an alcohol solution containing said diterpene glycosides; passing said alcohol solution through a second column containing an alkaline macroporous resin so as to provide a purified alcohol solution containing said diterpene glycosides; and drying said purified alcohol solution so as to provide a dry composition containing said diterpene glycosides.

The process of the present invention provides a dry composition final product which contains a high yield of diterpene glycosides, as well as certain beneficial and non-bitter tannins, while astringent or bitter tasting tannins and other undesirable and/or insoluble materials are removed and disposed of so as to be substantially absent in the final product.

BRIEF DESCRIPTION OF THE DRAWINGS

A detailed description of the process of the present invention follows, with reference to the attached figure, which schematically illustrates the process of the present invention.

DETAILED DESCRIPTION

The invention relates to a process for extracting diterpene glycosides from plant sources, and more particularly, to a process for obtaining such diterpene glycosides which advantageously provides a highly concentrated diterpene glycoside product which is substantially free of undesirable components including bitter-tasting tannins and insoluble matter.

Diterpene glycosides are present in a number of plant or herbal sources, especially members belonging to the Rosaceae family and the Ericaceae family, especially members of the Eubatus section of Rosaceae, most especially the Rubus species. Specific examples of plants containing excellent sources of diterpene glycosides include Eubatus section members. The Eubatus section includes more than 50 species and cultivated varieties of plants commonly referred to as blackberry and dewberry plants. Some specific examples are Chinese blackberry (Rubus Suavissimus), regular blackberry (Rubus fruticosus L.) raspberry (Rubus idaeus L. or Rubus strigosus M.) and blueberry (Vaccinium corymbosum L. or V. myrtillus L.)

Fruit, bark, branches and leaves of the aforesaid plants themselves are known and used as naturally-occurring and safe foods and herbs for various health benefits, and are traditionally used for treating sore throat, cough, mucus, thirst, blood pressure and for lowering of blood sugar, etc.

These plants contain natural sweetening agents, specifically diterpene glycosides and/or Rubusosides. Specifically, these plants contain the beta-D-glucosyl ester of 13-O-beta-D-glucosyl-steviol. These plants also include a wide variety of polyphenolic substances or tannins, some of which give health benefits and others of which have an astringent or bitter taste.

In accordance with the process of the present invention, plant source material, especially leaves and fruit of the aforesaid plants, are processed so as to extract a dry final composition which contains a high concentration of diterpene glycosides, and which is substantially free of bitter-tasting tannins. This product can advantageously be used as a naturally occurring, safe and economically prepared sweetener, and has a sweetness typically at least about 40, preferably between about 60 and about 100, and most preferably about 80 times the sweetness per unit weight of refined sugar.

In accordance with the process of the present invention, plant source material such as leaves, bark, branches and/or fruit of the aforesaid plants which contain diterpene glycosides are obtained and first subjected to a liquid extraction process, preferably by boiling in a bath of suitable material such as water, ethanol and the like. This liquid extraction process may preferably be carried out for a period of between about 1 and about 3 hours, and results in a liquid product containing extract from the plant source material including the desired diterpene glycosides. Following the initial liquid extraction process, a first volume or aliquot of liquid is obtained, and additional extractions may then be carried out, preferably at least 3 or 4 extractions, using additional boiling solutions. This results in a final combined liquid product which contains a large amount of diterpene glycosides originally included in the plant source material.

The liquid extract is then mixed with a saturated solution, and allowed to rest or settle in a conventional setting apparatus so as to provide a solid precipitate and a liquid portion containing soluble portions of the original liquid extract.

According to the invention, the saturated solution is preferably a solution saturated with at least one metallic ion having an oxidation number of 2 or 3. Preferred saturated solutions include solutions saturated with aluminum ion or calcium ion, or combinations thereof, most preferably aluminum ($Al^{+3}$).

Liquid extract and saturated solution may suitably be mixed in this step at a ratio by volume of liquid extract to saturated solution of between about 600:1 and about 100:1.

The liquid extract and saturated solution are preferably thoroughly mixed so as to provide a substantially homogeneous mixture, and then allowed to rest, preferably for a period of at least about ½ hour, more preferably for at least about 1 hour, and most preferably between about 1 and about 3 hours, until a solid precipitate material has formed, and a liquid portion can be removed from the upper areas of the settling vessel.

The solid precipitate contains certain portions of original starting plant source material which are undesirable in the end product, and this solid precipitate material can be disposed of or used for other purposes if desired.

The liquid portion following settling includes the desired diterpene glycosides and is then passed to a first column in accordance with the present invention. The first column is preferably an affinity column loaded with a neutral absorptive macroporous resin. The liquid portion is preferably fed to this column at a volumetric rate of between about 3 and about 15 volumes, preferably about 10 volumes of liquid feed per volume of the column. While passing through the first column, the diterpene glycosides of the liquid portion, as well as certain other material, are selectively absorbed onto the resin. The liquid material exiting the first column contains undesirable plant components for the present process, and can be disposed of or used for other processes, as desired.

Following the flow of liquid portion through the first column, the first column is then rinsed or flushed, preferably through several cycles, with an alcohol solution which removes the desired diterpene glycosides from the resin of the first column. The alcohol solution used for rinsing may suitably be an ethanol solution, preferably having a concentration of between about 70% and about 95%. The ethanol rinsing of the first column is preferably carried out through several cycles until ethanol passing from the column no longer has a sweet taste, thereby indicating that substantially all diterpene glycosides have been removed from the column. Typically, this may involved between about 2 and about 12 rinsing cycles, and is carried out so as to provide a ratio of total ethanol volume to volume of the column of between about 3:1 and about 6:1. It is preferred in this step to begin flushing using an ethanol solution having a relatively low concentration, preferably about 70%, and to gradually increase the concentration with each wash to a final wash using about 95% ethanol. This advantageously results in a more complete and efficient removal of the absorbed diterpene glycosides.

Following rinsing, the first column may be regenerated or reactivated, if necessary, using conventional techniques and is then ready for further use according to the invention.

The volume of ethanol solution recovered following rinsing of the first column now contains the desired diterpene glycosides, and this alcohol solution is then passed through a second column according to the invention where certain undesirable components are removed. According to the process of the present invention, the second column is an affinity column loaded with an alkaline macroporous resin. The alcohol solution is preferably fed to the second column at a volumetric rate per volume of the column of between about 3:1 and about 15:1, preferably a volumetric rate or ratio of alcohol solution volume to column volume of about 10:1. During treatment in the column, certain undesirable components, specifically the bitter tasting tannins of the original plant source material, are absorbed onto the resin. The resulting purified liquid product coming from the second column now includes alcohol and a highly purified diterpene glycoside product.

In accordance with the process of the present invention, this purified alcohol solution is then preferably dried, most preferably spray dried or vacuum spray dried at a temperature of between about 50° C. and about 150° C., so as to provide a final dry composition containing a high concentration of diterpene glycosides.

After treating the aforesaid volume of alcohol solution, the second column is preferably rinsed or otherwise treated or reactivated in accordance with conventional processes so as to remove the absorbed undesirable components and reactivate same for further use in continuing processes in accordance with the present invention.

According to the invention, the final dry composition preferably includes at least about 40% (wt) preferably at least about 60% (wt) and most preferably at least about 80% (wt) of diterpene glycosides, with the balance being certain non-bitter and desirable tannins and other acceptable soluble plant material. This composition typically has a sweetness or flavor profile having a sweetness which is about 80 times sweeter than a weight equivalent amount of refined sugar.

In accordance with the present invention, it has been found that the specific sequence of steps as set forth above is important if not critical in providing the desired high concentration of diterpene glycosides in the end product, and the substantial absence of bitter tasting tannins in same. The attached figure presents a schematic illustration of this process in accordance with the present invention. As shown, a plant source material 10 is initially fed to a bath 12 containing a boiling liquid for use in extracting certain components of the plant source material. As set forth above, bath 12 may suitably be a bath of boiling water, ethanol and the like, preferably at a temperature of between about 80° C. and about 100° C.

Liquid extract 14 exiting bath 12 is then mixed with a saturated solution 16, and the mixture fed to a settling tank 18 where a solid precipitate 20 is formed, as is a liquid solution 22 containing the desired diterpene glycosides. Liquid solution 22 is then fed to a first column 24, wherein diterpene glycosides and certain other material are absorbed, and a resulting liquid product 26 is then disposed of and/or discarded. An alcohol solution 28 is then fed through first column 24 so as to remove the absorbed diterpene glycosides and other materials, and the resulting alcohol solution 30 is then fed to a second column 32. In second column 32, the alkaline macroporous resin selectively absorbs bitter-tasting and undesirable tannins, while the remaining purified liquid portion 34 now contains highly purified diterpene glycosides, and is passed to a drier 36 wherein the solution is dried so as to provide the final dry composition 38 having a highly purified diterpene glycoside content preferably of at least about 80% (wt).

Second column 32 may suitably be treated after use so as to remove absorbed undesirable components 40 and prepare second column 32 for further use in accordance with the process of the present invention.

Of course, the illustration in the figure is a schematic and illustrates only one form of the process of the present invention. The process could be carried out using alternative structures and/or devices to perform the desired settling of solid material and selective absorptions which result in the desired highly purified diterpene glycoside product, well within the broad scope of the invention.

As set forth above, the initial plant source material may suitably be selected from a wide variety of materials, preferably from the group consisting of members of the Rosaceae family, members of the Ericaceae family, and combinations thereof. The preferred source material is Eubatus section members of the Rosaceae family, preferably Rubus species, and is most preferably selected from the group consisting of fruit, bark, branches and leaves of Rubus Suavissimus.

The neutral macroporous resin of the first column, and the alkaline macroporous resin of the second column for use in accordance with the present invention preferably has a surface area of between about 100 and about 1000 $m^2/g$. This is desirable so as to insure sufficient contact of the resin with various molecules in solution so as to obtain a desired selective absorption in each column.

The process of the present invention advantageously provides an efficient, simple, consistent and economic process for obtaining a high yield of diterpene glycosides. Further, at least about 90% of bitter-tasting materials such as polyphenolic compounds or tannins are removed, and the resulting product is clear, has no appreciable insoluble components, and has a pure sweet taste profile. Further, no organic or inorganic chemicals other than the saturated solution and ethanol are involved in the process. Thus, the process is safe and avoids environmental pollution.

An illustrative example of a process in accordance with the present invention is now presented in order to further illustrate the invention.

EXAMPLE 100 grams of dried blackberry leaves (Rubus Suavissimus) were added to 1000 ml of boiling water and boiled from 1 to 3 hours. The extract from this boiling was filtered through a stainless steel screen (40 mesh), and the leftover solid material was then extracted again using 800 ml of boiling water, and then 600 ml of boiling water for 3 extractions. The resulting total liquid volume following filtering and collection was 3000 ml, and this volume contains the desired diterpene glycosides from the starting source material, as well as other desirable and undesirable components. The 3000 ml liquid extract was then mixed with 10 ml of a saturated $Al^{+3}$ solution and mixed thoroughly. This mixture was then set to precipitate for 0.5 hours, and a solid precipitate developed as did a clear liquid portion carrying the desired diterpene glycosides. This clear liquid portion was then passed through an absorptive affinity chromatography column filled with 500 grams (300 ml) of neutral macroporous resin having a surface area of between about 400 and about 500 $m^2/g$. The resin was then washed using 1500 ml of a 70–95% ethanol solution until the product of the washing step did not contain a sweet taste. This washing was carried out in a first cycle using 500 ml of a 70% ethanol solution, followed by 500 ml of an 80% ethanol solution, and finally 500 ml of a 95% ethanol solution. The collected liquid following the washing of the first column was then passed through a second column containing 500 grams of alkaline macroporous resin which selectively absorbs certain undesirable components, particularly bitter-tasting tannins. The resulting purified liquid was then dried at 120° C. in a vacuum-spray drier and a fine white powder was obtained. This white powder yielded approximately 2.2 grams which contained approximately 80% diterpene glycoside, with the remaining 20% being non-bitter tasting tannins and other remaining acceptable plant material. The powder had a sweetness approximately 80 times more intense than equivalent amount of refined sugar.

It should be readily apparent that a process has been provided in accordance with the present invention which satisfies all desired objectives and provides a highly purified and clean sweet-tasting diterpene glycoside product.

It is to be understood that the invention is not limited to the illustrations described and shown herein, which are deemed to be merely illustrative of the best modes of carrying out the invention, and which are susceptible to modification of form, size, arrangement of parts and details of operation. The invention rather is intended to encompass all such modifications which are within its spirit and scope as defined by the claims.

What is claimed is:

1. A process for obtaining diterpene glycosides from a plant source containing diterpene glycosides, comprising the steps of:

providing a plant source material containing diterpene glycosides, obtaining a liquid extract from said source material, said liquid extract containing said diterpene glycosides;

mixing said liquid extract with a saturated solution containing at least one metallic ion selected from the group consisting of metallic ion having an oxidation number of three, metallic ions having an oxidation number of two, and combinations thereof to provide a mixture;

allowing said mixture to stand to permit a solid material to precipitate thereby providing said solid material and a liquid portion containing said diterpene glycosides;

passing said liquid portion through a first column containing a neutral absorptive macroporous resin to absorb portions of said liquid portion including said diterpene glycosides onto said neutral absorptive macroporous resin;

rinsing said first column with an alcohol to obtain an alcohol solution containing said diterpene glycosides;

passing said alcohol solution through a second column containing an alkaline macroporous resin so as to provide a purified alcohol solution containing said diterpene glycosides; and drying said purified alcohol solution so as to provide a dry composition containing said diterpene glycosides.

2. A process according to claim 1, wherein said source material is selected from the group consisting of members of the Rosaceae family, members of the Ericaceae family, and combinations thereof.

3. A process according to claim 1, wherein said source material is a member of the Eubatus section of Rosaceae.

4. A process according to claim 3, wherein said source material is a member of the Rubus species.

5. A process according to claim 1, wherein said source material is selected from the group consisting of the fruit, the bark, the branches and the leaves of Rubus Suavissimus.

6. A process according to claim 1, wherein said source material also contains bitter tannins, and wherein said dry composition is substantially free of said bitter tannins.

7. A process according to claim 6, wherein said step of passing said alcohol solution through said second column selectively absorbs said bitter tannins so as to provide said purified alcohol solution substantially free of said bitter tannins.

8. A process according to claim 1, wherein said dry composition contains at least about 40% (wt) of said diterpene glycosides.

9. A process according to claim 1, wherein said dry composition contains at least about 60% (wt) of said diterpene glycosides.

10. A process according to claim 1, wherein said dry composition contains at least about 80% (wt) of said diterpene glycosides.

11. A process according to claim 1, wherein said step of obtaining said liquid extract comprises boiling said source material in a bath selected from the group consisting of water, ethanol and mixtures thereof so as to provide said liquid extract.

12. A process according to claim 1, wherein said mixing step comprises mixing said liquid extract with a saturated solution containing aluminum ion, calcium ion and mixtures thereof.

13. A process according to claim 1, wherein said mixing step comprises mixing said liquid extract with a saturated solution of $Al^{+3}$.

14. A process according to claim 1, wherein said mixing step comprises mixing said liquid extract and said saturated solution at a ratio by volume of said liquid extract to said solution of between about 600:1 and about 100:1.

15. A process according to claim 1, wherein said neutral macroporous resin has a surface area of between about 100 $m^2/g$ and about 1000 $m^2/g$.

16. A process according to claim 1, wherein said alkaline macroporous resin has a surface area of between about 100 $m^2/g$ and about 1000 $m^2/g$.

17. A process according to claim 1, wherein said drying step is carried out in a vacuum-spray drier at a temperature of between about 50° C. and about 150° C.

18. A process according to claim 1, wherein said dry composition is at least about 40 times sweeter per unit weight than refined sugar.

19. A process according to claim 1, wherein said alcohol is an ethanol solution.

20. A process according to claim 19, wherein said ethanol containing solution has a concentration of ethanol of between about 70% v/v and about 95% v/v.

21. A process according to claim 20, wherein said rinsing step comprises a plurality of rinsing steps starting with a solution having an ethanol concentration of about 70% v/v and finishing with a solution having an ethanol concentration of about 95% v/v.

22. A process according to claim 1, wherein said step of obtaining said liquid extract comprises boiling said source material in a bath for at least about ½ hour.

23. A process according to claim 22, further comprising the step of repeating said boiling step for said source material with at least one additional bath.

* * * * *